United States Patent [19]
Hersh et al.

[11] 3,933,997
[45] Jan. 20, 1976

[54] SOLID PHASE RADIOIMMUNOASSAY OF DIGOXIN

[75] Inventors: Leroy S. Hersh, Painted Post; Sidney Yaverbaum, Big Flats, both of N.Y.

[73] Assignee: Corning Glass Works, Corning, N.Y.

[22] Filed: Mar. 1, 1974

[21] Appl. No.: 447,251

[52] U.S. Cl. .................... 424/1; 23/230 B; 424/12
[51] Int. Cl.² ........... A61K 43/00; G01T 1/16; G01T 1/167; G21H 5/02
[58] Field of Search ....... 23/230 B; 250/303; 424/1, 424/12

[56] References Cited
UNITED STATES PATENTS

| | | |
|---|---|---|
| 3,519,538 | 7/1970 | Messing et al. .................. 424/12 X |
| 3,652,761 | 3/1972 | Weetall ........................... 424/12 |

*Primary Examiner*—Benjamin R. Padgett
*Assistant Examiner*—Christine M. Nucker
*Attorney, Agent, or Firm*—James A. Giblin; Clinton S. Janes, Jr.; Clarence R. Patty, Jr.

[57] ABSTRACT

Clinically significant concentrations of digoxin can be determined by reacting an unknown amount of digoxin, a known amount of labelled digoxin, and a composite consisting of anti-digoxin antibodies coupled through an intermediate silane to magnetically responsive particles; magnetically separating the immunochemical complexes formed thereby, counting the radioactivity of either the separated products or remaining solution, and relating the count to a standard curve.

7 Claims, 2 Drawing Figures

SOLID PHASE RADIOIMMUNOASSAY OF DIGOXIN

BACKGROUND OF THE INVENTION

1. Field of the Invention

This invention relates generally to radioimmunoassay and specifically to solid phase radioimmunoassay of digoxin.

Radioimmunoassay (RIA) is a term used to describe any of several methods for determining very low concentrations of substances, which methods are based on the use of radioactively labelled substances which can form immunochemical complexes. The RIA of a substance for which there exists antibodies is based on the observation that an unknown amount of that substance will tend to compete equally with a known amount of that substance (radioactively labelled) for a limited number of complexing sites on antibodies to the substance. Thus, by permitting the above reaction, and separating the immunochemical complexes formed thereby from the reaction solution, the unknown concentration can be determined by relating the radioactivity count of the separated products or remaining solution to a standard curve prepared beforehand using known amounts of labelled and unlabelled substances.

An essential step in RIA is the separation of the immunochemical complexes from the reaction solution. To facilitate this step, various techniques have been devised to immobilize anti-substance antibodies on essentially water-insoluble carrier materials so that a relatively rapid separation can be accomplished with readily available equipment (e.g. a centrifuge). Methods for immobilizing antibodies on such carriers can be found in U.S. Pat. No. 3,555,143, (organic carriers) issued to Axen et al. on Jan. 12, 1971 and U.S. Pat. No. 3,652,761, (inorganic carriers) issued to H. H. Weetall on Mar. 28, 1972. When such carrier materials are used as supports for antibodies in RIA, it has become a common practice to refer to the technique as solid-phase RIA or, simply, SPRIA. The present invention discloses a novel SPRIA for digoxin.

Digoxin is a cardiac glycoside commonly used in very small quantities as a heart stimulant. The difference between therapeutic and toxic amounts of digoxin is often very slight. Thus, it is very important to have methods for accurately determining very small concentrations of digoxin in serum or plasma samples. Since the clinically significant concentration range of digoxin is within the broad range of about 0.5ng to about 10 ng per ml, RIA offers the only practical method for determining digoxin concentrations.

2. Description of Prior Art

Although conventional RIA techniques are known for measuring digoxin concentrations, those techniques are often time-consuming because they require relatively long periods of time for complete separation of digoxin-anti-digoxin antibody complexes. Hence, because of the importance knowing digoxin concentrations as rapidly as possible, attention has been made in recent years to develop a SPRIA for digoxin which would permit rapid separation and accuracy within the clinically significant concentration range. Methods for conjugating digoxin residues to the amino groups of lysine residues in human serum albumin are disclosed by T. W. Smith et al. in Biochemistry, 9, No. 2, 331–337 (1970) and by V. P. Bulter et al. in Proc. N.A.S., 57, 71–78 (1966). A method of labelling a digoxin derivative with $^{125}I$ is disclosed by Gutcho et al. in Clin. Chem. 19/9, 1058–59 (1973). As mentioned above, various techniques for coupling antibodies to inorganics through silanes are disclosed in U.S. Pat. No. 3,652,761, issued to H. H. Weetall. In those disclosures which disclose a specific SPRIA for digoxin, however, the methods of separating immunochemical complexes generally involve using a centrifuge. Although the use of a centrifuge facilitates separation and hastens obtaining the assay results, the use of a centrifuge does not readily permit instrumentation of the SPRIA of digoxin. Hence, there has been a need for another method of separating the reaction products of SPRIA which method could be readily instrumentized for quicker assay results.

In an article by P. J. Robinson et al in Biotech. Bioeng. XV, 603–606 (1973) there are suggested various techniques for separating immobilized enzymes by coupling the enzymes to magnetically responsive inorganic particles and then using magnetism to effect the separation. We are unaware, however, of the use of a similar technique to provide for magnetic separations in a SPRIA of digoxin, especially in a SPRIA of digoxin which can be successfully used to measure clinically significant amounts of digoxin. We have found that a successful SPRIA of digoxin is possible using magnetically responsive carrier materials. The SPRIA lends itself to instrumentation. Details of our composites and methods of making and using them are described below.

SUMMARY OF INVENTION

Our method for determining the concentration of digoxin, especially within the clinically significant concentration range of about 0.5 ng/ml to about 10 ng/ml., comprises the steps of:

A. reacting a solution containing an unknown amount of digoxin, a known amount of radioactively labelled digoxin, and composites consisting of anti-digoxin antibodies coupled chemically through an intermediate silane coupling agent to magnetically responsive inorganic particles to form immunochemical complexes;

B. magnetically separating the composites from the reaction solution;

C. counting the radioactivity of either the removed composites or the remaining solution; and D. relating the radioactivity count of step (C) to a standard to determine the digoxin concentration.

In a preferred embodiment, our method comprises using a composite consisting of anti-digoxin antibodies coupled through a silane coupling agent to $Fe_3O_4$ particles having an average particle size between about 1.5 and 10 microns, and having a surface area of at least about 10 m²/g,

SPECIFIC EMBODIMENTS

Figure 1:
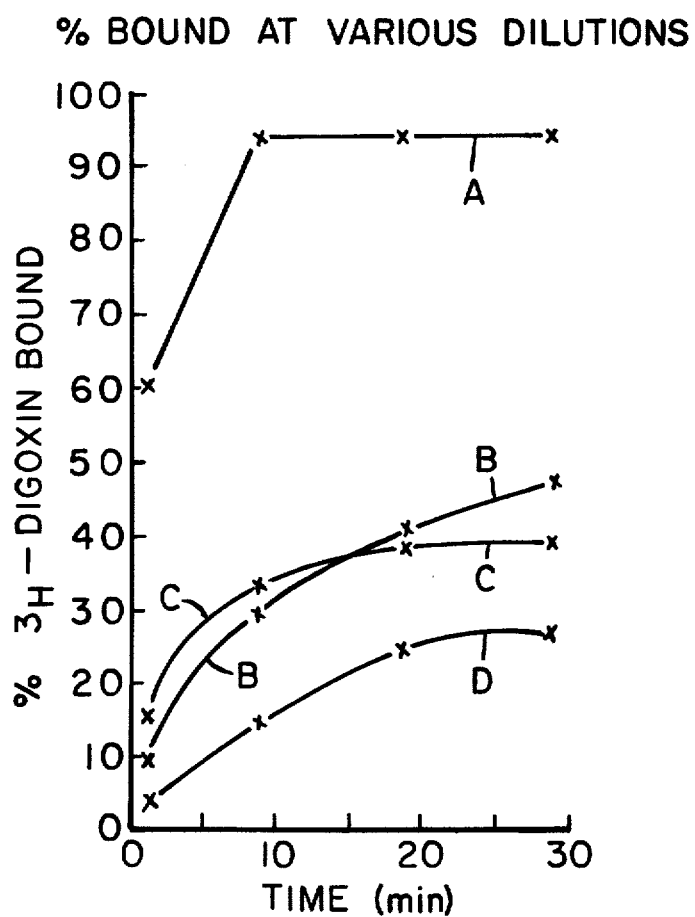
FIG. 1 is a graph illustrating the biological activity at various dilutions of magnetite-anti-digoxin antibody composites at ambient temperatures in the presence and absence of human plasma.

A very important aspect of our SPRIA of digoxin is the carrier for the anti-digoxin antibodies. The carrier must be magnetically responsive; that is, responsive to magnetic forces such that a suspension of carrier particles can be removed from a solution with the aid of a magnet, magnets, or magnetic forces. Further, the carrier must be capable of being silanized so that the anti-digoxin antibodies (antisera) can be coupled chemically through a silane to the carrier. As used herein, the term silanized, or its equivalent, refers to an inorganic carrier which has attached to the surface thereof compounds known as silanes and which compounds are capable, alone, or through modification, of reacting with anti-digoxin antibodies to chemically couple the antibodies to the carrier without significant loss of antibody complexing ability.

As shown in U.S. Pat. No. 3,652,761, (coupling of antibodies and antigenic substances to silanized inorganics) and U.S. Pat. No. 3,519,538. (coupling enzymes to silanized inorganics) the inorganic carrier materials should have available surface oxide or hydroxyl groups with which silanes can react for attachment of the silane. Since our carrier must be both magnetically responsive and capable of being silanized, it is contemplated that our SPRIA of digoxin can use anti-digoxin carriers of the following materials: $Fe_3O_4$, CoO, NiO, $Mn_2O_3$, and finely divided iron and nickel particles which have oxide surfaces. Such materials can be readily silanized by known means. In view of the various coupling techniques disclosed in U.S. Pat. No. 3,652,761, and this disclosure, those skilled in the art will be able to devise numerous methods of coupling active anti-digoxin antibodies by appropriately modifying the attached silanes for coupling with the antibodies in such a manner that the complexing ability of the coupled antibody is not lost.

In addition to the requirements of being magnetically responsive and capable of being silanized, our carriers should be essentialy water-insoluble and have a relatively high surface area (e.g. greater than about 10 $m^2/g$) to assure sufficient loading of anti-digoxin antibodies. Sensitivity of our SPRIA, especially in the clinically significant concentration range of digoxin, requires that such a relatively large surface area be available for antibody loading. Further, since immunochemical complexing is enhanced by assuring maxium exposure of the loaded antibody to the reaction or incubation solution, our average carrier particle size is such that the carrier-antibody composites will remain in suspension in the reaction solution for a period of time sufficient to assure enough complexing that will permit an accurate count and concentration determination (e.g. the particles should be small enough to remain in suspension for at least about 5 minutes). To achieve the above requirements, our carrier consists of silanizable, magnetically responsive inorganic particles having an average particle size between about $1.5\mu$ and about $10\mu$, preferably between about $1.5\mu$ and about $2.5\mu$.

In the illustrative examples below, anti-digoxin (goat) antiserum obtained from Biospheres, Inc. of Miami, Fla. and having a titer of at least 1:50,000, was coupled chemically through a diazotized silane coupling agent to particles of $Fe_3O_4$ as described in greater detail hereunder. The $Fe_3O_4$ particles were obtained from Fischer Scientific Co. (I-119, lot no. 765853) and consisted of purified $Fe_3O_4$ particles having a particle size distribution such that about 50% of the particles were equal to or slightly larger than $2.5\mu$. Substantially all the particles had a size between about 1.5 and 10 microns.

The particles were silanized by using an arylamine trimethoxy silane (Union Carbide Y-5475). The silanized carrier was then diazotized and coupled to the anti-digoxin antiserum, as indicated. Biological activity (or complexing ability) of the resulting composites were then determined and a typical standard curve (standard) was prepared as described, using $^3$H-Digoxin (tritiated digoxin).

Preparation of Arylamine-Magnetite

One ml of arylamine trimethoxy silane (Union Carbide Y-5475) was dissolved in 100 ml of $CH_3OH$. Then 10 ml of distilled water and 0.4 g of orthophosphorous acid [$H_2(HPO_3)$] were added and the solution was stirred for 15 minutes. Finally, 2 gms of the above-described $Fe_3O_4$ particles were added and the suspension was swirled for 2 hours. The solution was decanted and the silanized $Fe_3O_4$ particles were blotted dry before vacuum drying at 90°C for 24 hours. The silanized $Fe_3O_4$ was then rinsed three times with $CH_3OH$ and air dried.

Preparation of Magnetite-Digoxin Antiserum Composite

To 2g of arylamine-magnetite wet cake (ice-cold) were added with stirring, 10 ml of 2N HCl and 0.25 g of solid $NaNO_2$. The reaction mixture was placed in a vacuum desiccator for 40 minutes. The diazotized magnetite was washed and added in increments to 1.5 ml goat anti-digoxin serum, previously adjusted to pH 8.3 with 0.1 N NaOH. The coupling procedure was performed in an iced test tube, and the pH was maintained between 7.5 and 8.5 with 0.1 N NaOH. The reaction was continued for 2 hours in this manner. The pH was at 8.5 for the last 30 minutes. The reaction mixture was refrigerated overnight. The mixture was washed four times with borate buffered saline (BBS-0.01 M Borate, pH 8.5, in 0.15M-NaCl) and stored as a wet cake at 5°C.

Analysis of the wet cake showed that it was 46.3% dry weight and contained 11.7 mg protein/g dry weight of magnetite (as determined by Ninhydrin nitrogen determination procedure).

A suspension of 1.97 mg of the magnetite-antiserum IMA (immobilized antiserum) wet cake was made in 4 ml of 0.01 M PBS-BSA buffer (0.01 M phosphate, pH 7.4, in 0.15 M NaCl containing 3.5 mg bovine serum albumin and 0.0002% $NaN_3$). This was equivalent to 266.76 $\mu$g antiserum protein and 22.8 mg of IMA (dry weight) per ml of buffer suspension. The above is referred to herein as the stock suspension.

The sedimentation rate was measured without the presence of a magnetic field. The absorbance at 500 nm was followed after adding a mixed suspension into a cuvette. The absorbance decreased to about 20% of the initial value in 14 minutes. The $t_{1/2}$ was 5 minutes.

Determination of Biological Activity

An experimental protocol was prepared to test the IMA for biological activity. Portions of the above stock suspension were brought to ambient temperature and diluted 1:25, 1:50 and 1:100 in filtered distilled water (FDW). The protocol shown in Table 1 is a combination of two experiments.

The experiments were performed by placing all protocol reagents except the $^3$H-Digoxin into each of 5 tubes with stirring. All assay tubes were activated by the addition of $^3$H-Digoxin at one time. The reaction of one tube of each IMA dilution was terminated 7.5, 17.5 and 27.5 minutes after delta zero time (1.25 minutes). All tubes were stirred every 10 minutes. Termination of the reaction and separation of bound from free $^3$H-Digoxin was effected by holding the butt of the reaction test tube to a powerful magnet for 45 seconds. The magnet was an Alnico V magnet obtained from Edmund Scientific Co., said to be capable of lifting about 150 lbs. The supernatant solution was decanted into a scintillation vial containing 10 ml of Insta-Gel (Packard Corp.) while still holding the reaction tube butt to the magnet. The vials were counted for 1 minute in a Packard Tri-Carb Liquid Scintillation Spectrometer, Model 3320.

TABLE I

Experimental Protocol for the Determination of Biological Activity at Ambient Temperature of a Preparation of Digoxin Antiserum Immobilized on Magnetite

| Sample Content | Dilution of Stock Suspension | IMA Final Concentration Antiserum Protein mg | Dry Weight of IMA mg | FDW, ml. | Human Plasma ml. | IMA, ml. | $^3$H-Digoxin* ml. |
|---|---|---|---|---|---|---|---|
| Radioactive Antigen | | | | | | | |
| Control: 1. | — | — | — | 0.8 | — | — | 0.2 |
| 2. | — | — | — | 0.6 | 0.2 | — | 0.2 |
| Stock Suspension | Undiluted | 53.350 | 4.560 | 0.6 | — | 0.2 | 0.2 |
| Stock Suspension | 1:25 | 2.130 | 0.1825 | 0.4 | 0.2 | 0.2 | 0.2 |
| Stock Suspension | 1:50 | 1.065 | 0.0913 | 0.6 | — | 0.2 | 0.2 |
| Stock Suspension | 1:100 | 0.534 | 0.0450 | 0.6 | — | 0.2 | 0.2 |

*0.64 ng $^3$H-Digoxin and 5 nci/0.2 ml.
Experiment No. 2.

The results of the experiment are shown on FIG. 1 which illustrates the biological activity of the magnetite-digoxin antiserum at ambient temperature in the presence and absence of human plasma. In FIG. 1, A represents the undiluted (1:5 final) sample, B represents the 1:50 dilution (1:250 final), C represents the 1:25 (1:125 final) dilution in the presence of human plasma, and D represents the 1:100 (1:500 final) sample dilution. Good activity was demonstrated for all dilutions. However, because sensitivity and standard curve data would be collected in the presence of human plasma, the 1:25 (1:125 final dilution) suspension was selected for preparing a standard curve. The higher IMA dilutions would probably show lower binding capacities in the presence of human plasma (see FIG. 1) at 17.5 minutes reaction time. This would not be advantageous for the assay.

Standard Curve

A dilution of 1:25 of the stock solution was selected to prepare the standard curve in the presence of human plasma. The protocol for the standard curve was similar to the one shown in Table 1 (Experiment No. 2) with the addition that concentrations of unlabeled digoxin (0.5, 1.0, 2.0, 5.0 and 10.0 mg/ml) in human plasma were included. The digoxin standard tubes were prepared in duplicate by adding 0.2 ml of filtered normal plasma containing known concentrations of digoxin to 0.4 ml of filtered distilled water, followed by 0.2 ml of the 1:25 dilution of IMA. Controls contained only the filtered distilled water and normal human plasma. Mixtures were stirred with each addition. Tubes were activated at 1 minute intervals by the addition of 0.2 ml of $^3$H-Digoxin (containing 0.64 ng digoxin and 5 nci activity as soon after the other reagents had been added. With the addition of $^3$H-Digoxin, each tube contained a 1.0 ml total volume. All tubes were stirred at 5 minute intervals. Reaction time was 17.5 minutes. Termination of the reaction and separation of the bound and free phases was effected by sedimentation and decantation in a magnetic field with the large magnet. The supernatant liquid was mixed with 10 ml of Insta-Gel in a scintillation vial and counted on the Packard Model 3320 for 1 minute.

Figure 2:
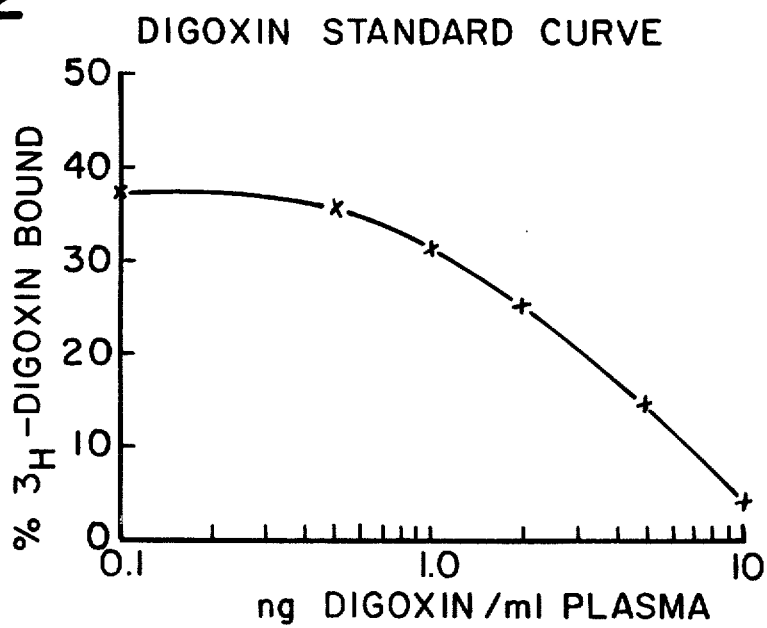
FIG. 2 is a graph illustrating a standard digoxin assay curve generated using one of our composites.

Results of the experiments are summarized in Table 2, and graphically demonstrated in FIG. 2. The data show a Δ% binding of 33% and a slope of 0.845. The immobilized antiserum preparation had 47% of the native antibody activity of the soluble antiserum (1:70,000 dilution of goat anti-digoxin serum, 70 mg protein/ml) on a protein weight basis.

TABLE 2

Standard Curve Data for Digoxin Antiserum - Magnetite Composite.*

| Sample | | cpm | % Free Digoxin | % Bound Digoxin |
|---|---|---|---|---|
| 3H-Digoxin Control | | 3990 | 100.0 | 0.0 |
| 0 ng | Digoxin/ml Plasma | 2514 | 63.0 | 37.0 |
| 0.5 | " | 2579 | 64.7 | 35.3 |
| 1.0 | " | 2725 | 68.3 | 31.7 |
| 2.0 | " | 3002 | 75.2 | 24.8 |
| 5.0 | " | 3390 | 85.0 | 15.0 |
| 10.0 | " | 3836 | 96.2 | 3.8 |

Ambient temperature, 17.5 minutes reaction time.
*2.13 μg Antiserum protein/182.5 μg of complex.

The above experiments indicate that clinically significant concentrations of digoxin can be determined quickly and accurately using our magnetically separable antibody-carrier-composite. A workable standard curve was obtained in the range of 1 to 10 ng digoxin per ml of plasma. The protein loading was a respectable 1% (dry weight) for a nonporous body having a high surface area. Inasmuch as our illustrative methods and composites can be readily modified given the disclosure herein, it is intended that the above examples should be construed as merely illustrative and the scope of the present invention be limited only by the appended claims.

We claim:
1. A method of determining the concentration of digoxin in a solution comprising the steps of:
   A. reacting the solution, a known amount of radioactively labelled digoxin, and a composite consisting of anti-digoxin antibodies coupled chemically through an intermediate silane coupling agent to magnetically responsive inorganic particles, to form immunochemical complexes;
   B. magnetically separating the composite from the reaction solution;
   C. counting the radioactivity of either the removed composite or the remaining solution; and
   D. relating the count of step (C) to a standard to determine the digoxin concentration.

2. The method of claim 1 wherein the magnetically responsive particles are selected from the group consisting of $Fe_3O_4$, CoO, NiO, $Mn_2O_3$, finely divided iron particles, and finely divided nickel particles.

3. The method of claim 2 wherein the particles have an average particle size between about $1.5\mu$ and about $10\mu$.

4. The method of claim 2 wherein the particles have a surface area of at least 10 $m^2/g$.

5. The method of claim 1 wherein the composite of step (A) consists of the reaction product of anti-digoxin antibodies and silanized particles of $Fe_3O_4$ which, prior to the reaction with the antibodies, had been diazotized.

6. The method of claim 1 wherein the inorganic particles consist of $Fe_3O_4$ having an average particle size between about 1.5 and about $10\mu$.

7. An immunochemical composite suitable for use in determining clinically significant concentrations of digoxin and comprising anti-digoxin antibodies chemically coupled through an intermediate silane coupling agent to particles of $Fe_3O_4$ having an average particle size between about 1.5 and about 10 microns.

* * * * *

UNITED STATES PATENT OFFICE
CERTIFICATE OF CORRECTION

PATENT NO. : 3,933,997
DATED : January 20, 1976
INVENTOR(S) : Leroy S. Hersh and Sidney Yaverbaum It is certified that error appears in the above-identified patent and that said Letters Patent are hereby corrected as shown below:

Table 1, Columns 5 and 6, line 25, under heading Dilution of Stock Suspension, "1:25" should be -- 1:25# --.

Table 1, Columns 5 and 6, line 29, "Experiment No. 2." should be -- #Experiment No. 2. --.

Table 2, Column 6, line 30, "Standard Curve Data for Digoxin" should be -- Standard Curve # Data for Digoxin --.

Table 2, Column 6, line 38, "Ambient temperature, 17.5 minutes reaction time." should be -- #Ambient temperature, 17.5 minutes reaction time.--.

Signed and Sealed this

Tenth Day of August 1976

[SEAL]

Attest:

RUTH C. MASON
*Attesting Officer*

C. MARSHALL DANN
*Commissioner of Patents and Trademarks*